US006509186B1

(12) United States Patent
Zou et al.

(10) Patent No.: US 6,509,186 B1
(45) Date of Patent: Jan. 21, 2003

(54) MINIATURIZED THERMAL CYCLER

(75) Inventors: Quanbo Zou, Singapore (SG); Uppili Sridhar, Singapore (SG); Yu Chen, Singapore (SG); Tit Meng Lim, Singapore (SG); Emmanuel Selvanayagam Zachariah, Singapore (SG); Tie Yan, Singapore (SG)

(73) Assignee: Institute of Microelectronics, Singapore (SG)

( * ) Notice: Subject to any disclaimer, the term of this patent is extended or adjusted under 35 U.S.C. 154(b) by 95 days.

(21) Appl. No.: 09/846,126

(22) Filed: May 1, 2001

Related U.S. Application Data

(63) Continuation-in-part of application No. 09/785,588, filed on Feb. 16, 2001, now Pat. No. 6,432,695.

(51) Int. Cl.[7] .................................... C12M 1/36

(52) U.S. Cl. .................... 435/286.1; 435/287.2; 435/288.4; 422/109

(58) Field of Search .................... 435/286.1, 287.2, 435/287.3, 288.3, 288.4, 289.1, 303.1, 305.2; 422/102, 109, 113, 131; 216/2

(56) References Cited

U.S. PATENT DOCUMENTS

| | | | | |
|---|---|---|---|---|
| 5,589,136 A | | 12/1996 | Northrup et al. | 422/102 |
| 5,639,423 A | | 6/1997 | Northrup et al. | 122/50 |
| 5,646,039 A | | 7/1997 | Northrup et al. | 435/287.2 |
| 5,674,742 A | | 10/1997 | Northrup et al. | 435/286.5 |
| 5,716,842 A | | 2/1998 | Baier et al. | 435/283.1 |
| 5,939,312 A | | 8/1999 | Baier et al. | 435/287.2 |
| 6,344,325 B1 | * | 2/2002 | Quake et al. | 435/286.6 |
| 6,379,929 B1 | * | 4/2002 | Burns | 435/91.1 |
| 6,432,695 B1 | * | 8/2002 | Zou et al. | 435/287.2 |

OTHER PUBLICATIONS

P.F. Man, et al., (U. Michigan), "Microfabricated Capillary-Driven Stop Valve and Sample Injector", IEEE MEMS '98 (Provisional), pp. 45–50.

Ajit M. Chaudhari, et al., (Stanford Univ. and PE Applied Bio–systems), (1998), "Transient Liquid Crystal Thermometry of Mic Fabricated PCR Vessel Arrays", J. Micrelectromech. Sys. ,vol. 7, No. 4., pp. 345–355.

Mark A. Burns, et al., (U.Michigan), "An Integrated Nanolite DNA Analysis Device", Science 16, Oct. 1998, vol. 282, pp. 484–48.

Sundaresh N. Brahmasandra, et al., (U.Michigan), "On–Chip D Band Detection in Microfabricated Separation Systems", SPI Conf. Microfabricated Devices and Systems, Santa Clara, CA, Sep. 1998, SPIE vol. 3515, pp. 242–251.

S. Poser, et al., "Chip Elements for Fast Thermocycling", Euro sensors X. Leuven, Belgium, Sep. 1996, pp. 1197–1199.

(List continued on next page.)

*Primary Examiner*—David A. Redding
(74) *Attorney, Agent, or Firm*—George O. Saile; Stephen B. Ackerman

(57) ABSTRACT

The invention describes a thermal cycler which permits simultaneous treatment of multiple individual samples in independent thermal protocols, so as to implement large numbers of DNA experiments simultaneously in a short time. The chamber is thermally isolated from its surroundings, heat flow in and out of the unit being limited to one or two specific heat transfer areas. All heating elements are located within these transfer areas and at least one temperature sensor per heating element is positioned close by. Fluid bearing channels that facilitate sending fluid into, and removing fluid from, the chamber are provided. The chambers may be manufactured as integrated arrays to form units in which each cycler chamber has independent temperature and fluid flow control. Two embodiments of the invention are described together with a process for manufacturing them as well as two schemes for making connections to the outside world.

8 Claims, 10 Drawing Sheets

OTHER PUBLICATIONS

Adam T. Wooley et al., (UC Berkeley), "Functional Integratio PCR Amplification and Capillary Electrophoresis in a Microfabr DNA Analysis Device", Analytical Chem., vol. 68, pp. 4081–4086.

M. Allen Northrup, et al., (Lawrence Livermore Nat.'l Lab, Berkeley, Roche Molecular Systems), "DNA Amplification With Microfabricated Reaction Chamber", 7th Int'l. Conf. Solid–Sensors and Actuators, pp. 924–926.

* cited by examiner

MINIATURIZED THERMAL CYCLER

This is a continuation-in-part of IME2000-007, Ser. No. 09/785,588, filing date Feb. 16, 2001 assigned to a common assignee now U.S. Pat. No. 6,432,695.

The invention relates to the general field of MEMS with particular reference to thermal cycling chambers for use in, for example, polymerase chain reactions as well as other reactions that involve thermal cycling.

FIELD OF THE INVENTION

PCR (Polymerase Chain Reaction) is a molecular biological method for the in-vitro amplification of nucleic acid molecules. The PCR technique is rapidly replacing many other time-consuming and less sensitive techniques for the identification of biological species and pathogens in forensic, environmental, clinical and industrial samples. PCR using microfabricated structures promises improved temperature uniformity and cycling time together with decreased sample and reagent volume consumption.

BACKGROUND OF THE INVENTION

An efficient thermal cycler particularly depends on fast heating and cooling processes and high temperature uniformity. Presently, microfabricated PCR is preferably carried out on a number of samples during a single thermal protocol run. It is a great advantage if each reaction chamber can be controlled to have an independent thermal cycle. This makes it possible to run a number of samples with independent thermal cycles simultaneously (parallel processing). The first work on multi-chamber thermal cyclers fabricated multiple reaction chambers by silicon etching. Although separate heating elements for every reaction chamber can be realized, it was impossible in these designs to eliminate thermal cross-talk between adjacent reaction chambers during parallel processing because of limited thermal isolation between reaction chambers. As a result, multiple chambers having independent temperature protocols could not be used. Additionally, temperature uniformity achieved inside the reaction chamber was ±5 K in this thermal isolation and heating scheme.

Integration of the reaction chamber with micro capillary electrophoresis (CE) is also an interesting subject, in which small volumes of samples/reagents will be required both for PCR and CE. Again, a high degree of thermal isolation is very important particularly where various driving/detection mechanisms prefer a constant room temperature substrate.

A number of microfabricated PCR devices have been demonstrated in the literature. Most of them were made of silicon and glass, while a few others were using silicon bonded to silicon. On-chip integrated heaters and temperature sensors become important in the accurate control of the temperature inside these small reaction chambers. Good thermal isolations have been proved promising for quick thermal response. Micro reaction chamber integrated with micro CE was only demonstrated where no PCR thermal cycling was performed (only slowly heated to 50° C. in 10–20 seconds and held for 17 minutes). Parallel processing microfabricated thermal cyclers with multi-chamber and independent thermal controls have not yet been reported.

A routine search of the prior art was performed with the following references of interest being found: Northrup et al. (U.S. Pat. No. 5,589,136 December 1996), Northrup et al. (U.S. Pat. No. 5,639,423, U.S. Pat. No. 5,646,039, and U.S. Pat. No. 5,674,742), and Baier Volker et al, in U.S. Pat. No. 5,716,842 February 1998), did early work on multi-chamber thermal cyclers fabricated by silicon etching. Baier et al. (U.S. Pat. No. 5,939,312 August 1999) describe a miniaturized multi-chamber thermal cycler. This latter reference includes the following features—1. multiple chambers placed together within a silicon block from which they are thermally isolated. This approach works against fast cycling because of slow cooling by the chambers. 2. The chambers are packed together very closely, with minimal thermal isolation from one another, so all chambers must always to be thermally cycled with the same thermal protocol. The individual chambers were not subject to independent thermal control of multi-chambers. 3. Baier's units have thin-film heaters that cover the whole bottom of the chamber (as in conventional heating designs). 4. Baier's apparatus is limited to the chambers, no micro-fluidic components (valves, fluidic manipulation, flow control, etc.) being included.

Micro-fabricated PCR reaction chambers (or thermal cyclers) have been reported in the technical literature by a number of experimenters, including: (1). Adam T. Woolley, et al, (UC Berkeley), "Functional Integration of PCR Amplification and Capillary Electrophoresis in a Microfabricated DNA Analysis Device", Analytical Chemistry, Vol. 68, pp. 4081–4086, (2). M. Allen Northrup, et al, (Lawrence Livermore National Lab, UC Berkeley, Roche Molecular Systems), "DNA Amplification with a microfabricated reaction chamber", 7th Intl. Conf. Solid-State Sensors and Actuators, pp. 924–926, (3). Sundaresh N. Brahmasandra, et al, (U. Michigan), "On-Chip DNA Band Detection in Microfabricated Separation Systems", SPIE Conf. Microfuidic Devices and Systems, Santa Clara, Calif., September 1998, SPIE Vol. 3515, pp. 242–251, (4). S. Poser, et al, "Chip Elements for Fast Thermocycling", Eurosensors X, Leuven, Belgium, September 96, pp.11971199. The latter showed promising results for use of well thermal isolation as a means for achieving quick thermal response.

Also of interest, we may mention: (5). Ajit M. Chaudhari, et al, (Stanford Univ. and PE Applied Biosystems), "Transient Liquid Crystal Thermometry of Microfabricated PCR Vessel Arrays", J. Microelectromech. Systems, Vol. 7, No. 4, 1998, pp. 345–355, (6). Mark A Burns, et al, (U Michigan), "An Integrated Nanoliter DNA Analysis Device", Science 16, October 1998, Vol. 282, pp. 484–486, and (7). P. F. Man, et al, (U. Michigan), "Microfabricated Capillary-Driven Stop Valve and Sample Injector", IEEE MEMS'98 (provisional), pp. 45–50.

SUMMARY OF THE INVENTION

It has been an object of the present invention to provide a microfabricated thermal cycler which permits simultaneous treatment of multiple individual samples in independent thermal protocols, so as to implement large numbers of DNA experiments simultaneously in a short time.

A further object of the invention has been to provide a high degree of thermal isolation for the reaction chamber, where there is no cross talk not only between reaction chambers, but also between the reaction chamber and the substrate where detection circuits and/or micro fabricated Capillary Electrophoresis units could be integrated.

Another object has been to achieve temperature uniformity inside each reaction chamber of less than ±0.5 K together with fast heating and cooling rates in a range of 10 to 60 K/s range.

These objects have been achieved by use of a thermal isolation scheme realized by silicon etch-through slots in a supporting silicon substrate frame. Each reaction chamber is thermally isolated from the silicon substrate (which is also a heat sink) through one or more silicon beams with fluid-bearing channels that connect the reaction chamber to both a sample reservoir and a common manifold. Each reaction chamber has a silicon membrane as its floor and a glass sheet as its roof. This reduces the parasitic thermal capacitance and meets the requirement of low chamber volume. The advantage of using glass is that it is transparent so that sample filling and flowing can be seen clearly. Glass can also be replaced by any kind of rigid plastic which is bio- and temperature-compatible.

DESCRIPTION OF THE PREFERRED EMBODIMENTS

The basic principle that governs the present invention is that the thermally conductive cycler chamber is thermally isolated from its surroundings except for one or more heat transfer members through which all heat that flows in and out of the chamber passes. Consequently, by placing at least one heating element in each transfer area, heat lost from the chamber can be continuously and precisely replaced, as needed. This is achieved by placing, within the chamber, at least one temperature sensor per heating element and locating this sensor close to the heating elements. Additionally, by connecting the heat transfer areas to a heat sink through a high thermal conductance path, the chamber can also be very rapidly cooled, when so desired.

Also included as part of the structure of the present invention is a fully integrated fluid dispensing and retrieval system. This allows multiple chambers to share both a common heat sink as well as an inlet fluid source reservoir with both fluid flow and temperature being separately and independently controllable. As a result, thermal cross-talk between chambers can be kept to less than about 0.5° C. at a temperature of about 95° C. while temperature uniformity within an individual chamber can be reliably maintained, both theoretically and experimentally, to a level of less than ±0.3 K.

We now disclose two embodiments of the present invention as well as a process for manufacturing part of the structure.

First Embodiment

Figure 1A:
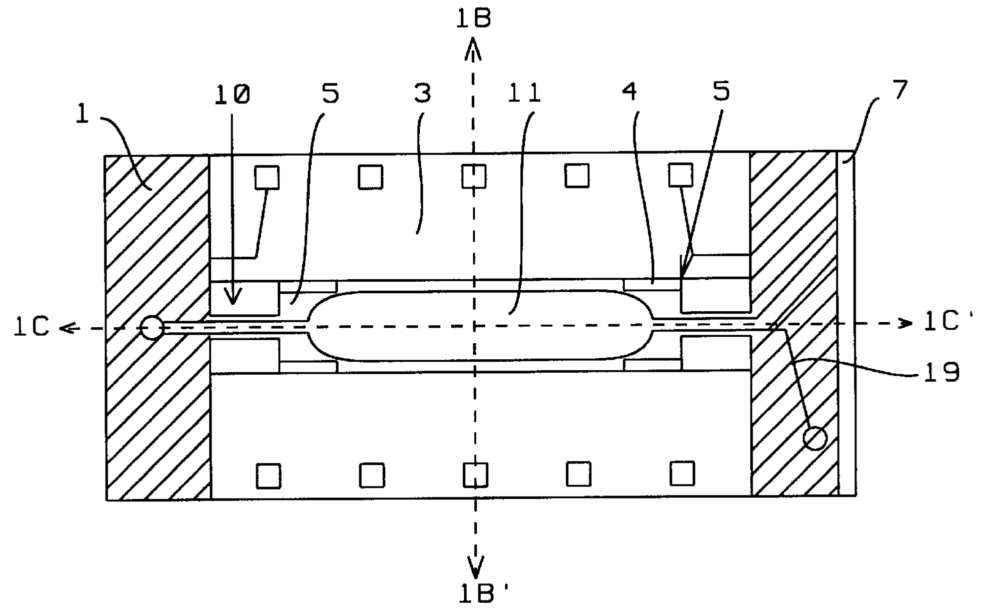
FIG. 1*a* shows a plan view of a first embodiment of the invention.

Referring now to FIG. 1*a*, the top-left portion is a plan view of the structure. Seen there is chamber 11 which is connected at both ends to silicon frame 1 through monocrystalline silicon beams 10. Heaters 5 are at each end inside the heat transfer areas. The latter are discussed above but are not explicitly shown since they have been introduced into the description primarily for pedagogical purposes. In addition to the heaters, each chamber contains at least one temperature sensor 4 for each heating element 5. They are located close to the heating elements, as shown.

Fluid bearing channels dispense fluid into and remove fluid from the chamber 11. They are brought into the chamber through the silicon beams 10. As can be more clearly seen in the closeup shown in FIG. 2, unprocessed fluid is stored in common reservoir 7 and is directed to chamber 11 through fluid-bearing channel 31. Control of fluid flow is achieved by use of compressed gas (usually, but not necessarily, air), or hydraulic/pneumatic pressure with a gas-liquid interface at the valve, that connects gas source 25 to channel 31 through air injector 19. Since the capillary force drives the fluid from reservoir 7 to valve 8 (FIG. 3), stopping there, an additional pressure impulse will help the fluid to pass through valve 8 and, after that, no more external pressure is needed as the fluid will continue to flow, being driven by capillary forces.

Figure 1B:
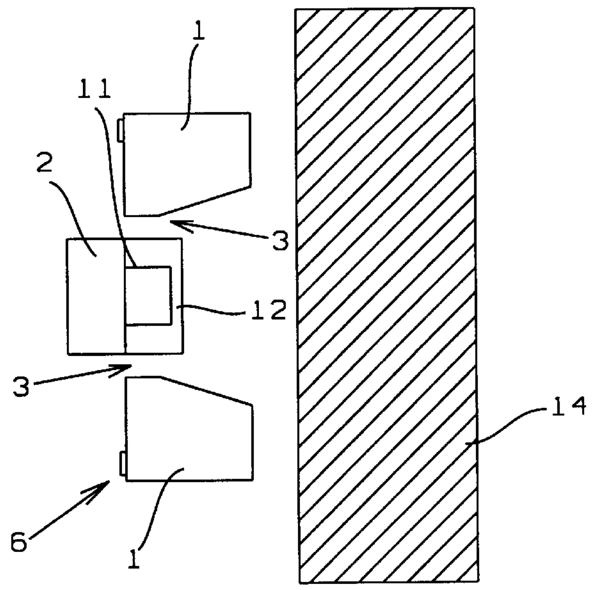
FIGS. 1*b* and 1*c* are orthogonal cross-sections taken through FIG. 1*a*.
Figure 1C:
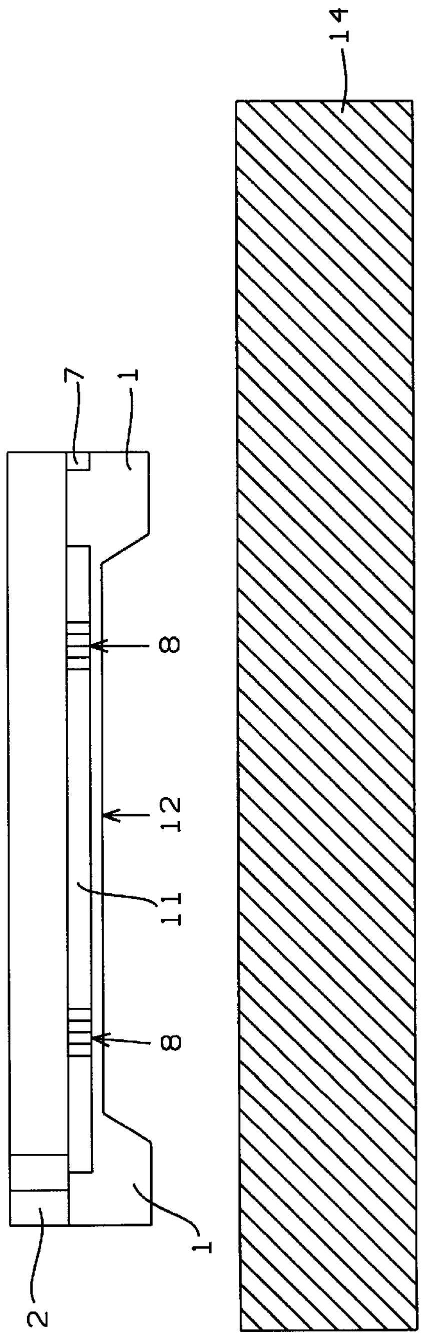
Figure 2:
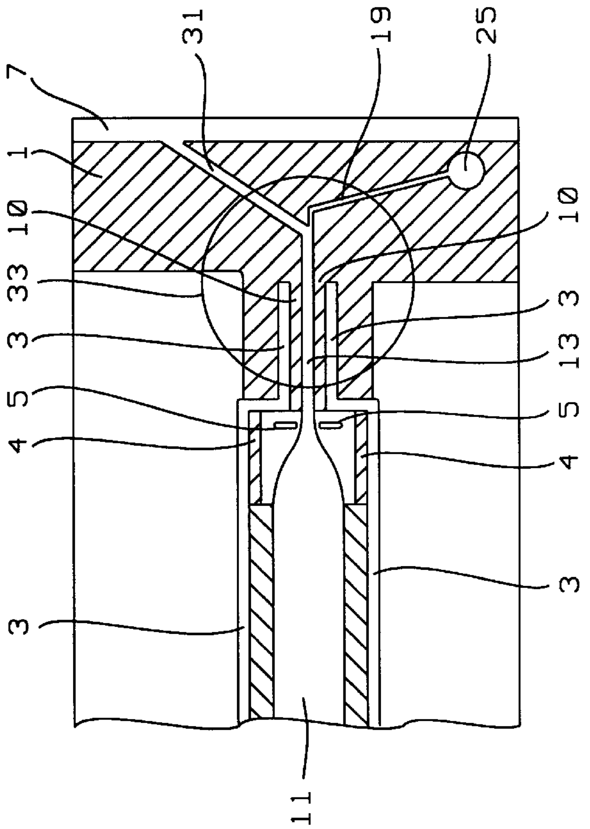
FIG. 2 is a closeup view of a portion of FIG. 1*a*.
Figure 3:
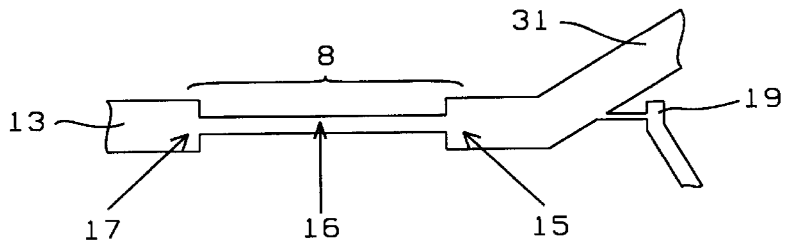
FIG. 3 illustrates the air injector and pressure valve part of the structure.

To prevent unintended entry of fluid into the chamber, pressure valves 8, as seen in FIG. 1*c*, are placed at both ends of the chamber. A closeup of the area contained within circle 33 of FIG. 2 is shown in FIG. 3 to illustrate how the valves operate. A short length 16 of the fluid-bearing channel is made narrower than the rest of the channel. When fluid coming from the right side reaches point 15 it will be drawn into 16 through surface tension (capillary action) if it wets the inside of the channel (i.e. channel walls are hydrophilic). Then, when the fluid reaches point 17, the same surface tension forces that drew the fluid into 16 will act to hold it inside 16 and prevent it from proceeding down channel 13. If the fluid finds the channel walls to be hydrophobic, then surface tension will act to keep it from entering 16. Either way, additional pressure is needed to make the fluid pass through valve 8. The recorded pressure barriers for water (about 6 kPa for valves, >10 kPa for the air injector) are enough to allow on-chip automatic control of fluid flow.

Returning now to FIG. 1*a*, the fluid-bearing channel on the far side of chamber 11 is seen to terminate at local reservoir 9. When fluid is forced into chamber 11, the air that is already in the chamber is forced out and passes into local (sample) reservoir 9 where it is allowed to escape but without allowing any liquid to enter it. When temperature cycling has been completed, pressure for the air injector is used to transfer the sample from the chamber into reservoir 9 where it can be collected into a pipette/tube or other collector.

Figure 4:
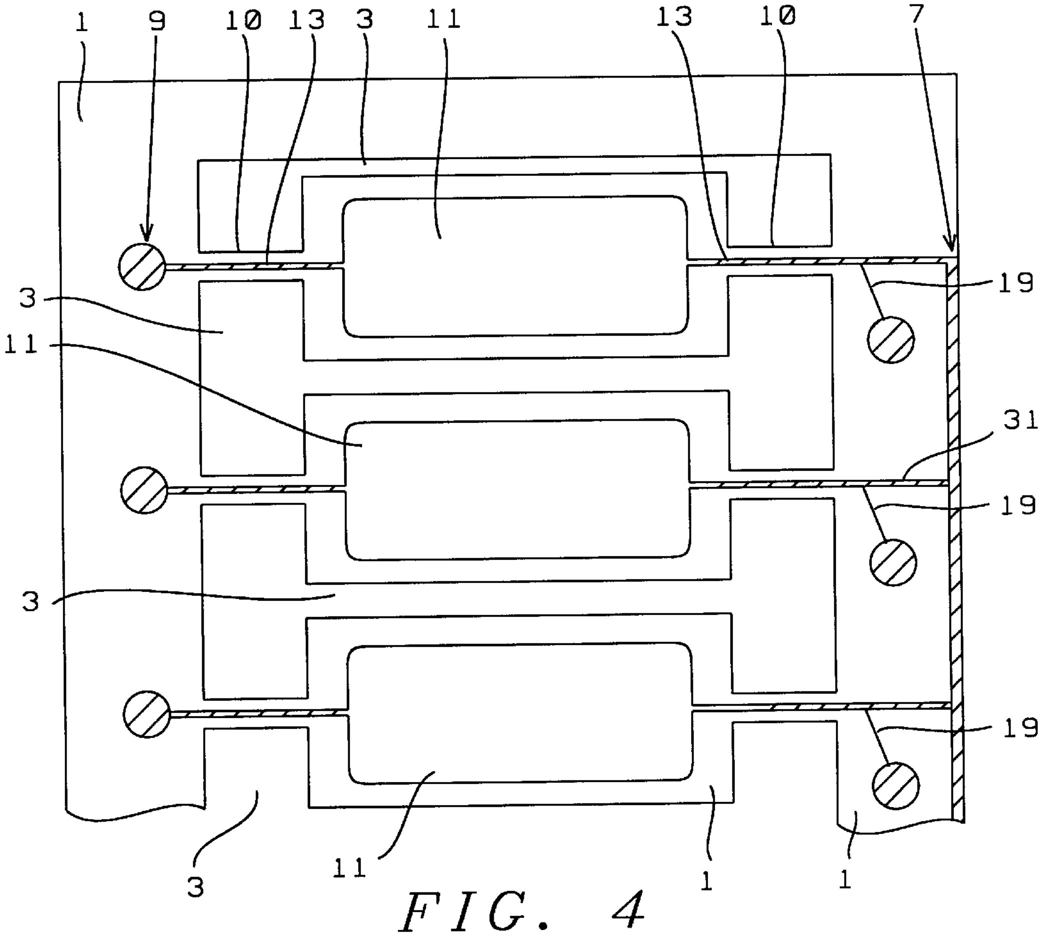
FIG. 4 shows a group of three cycling chambers integrated within a single unit.
Figure 5:
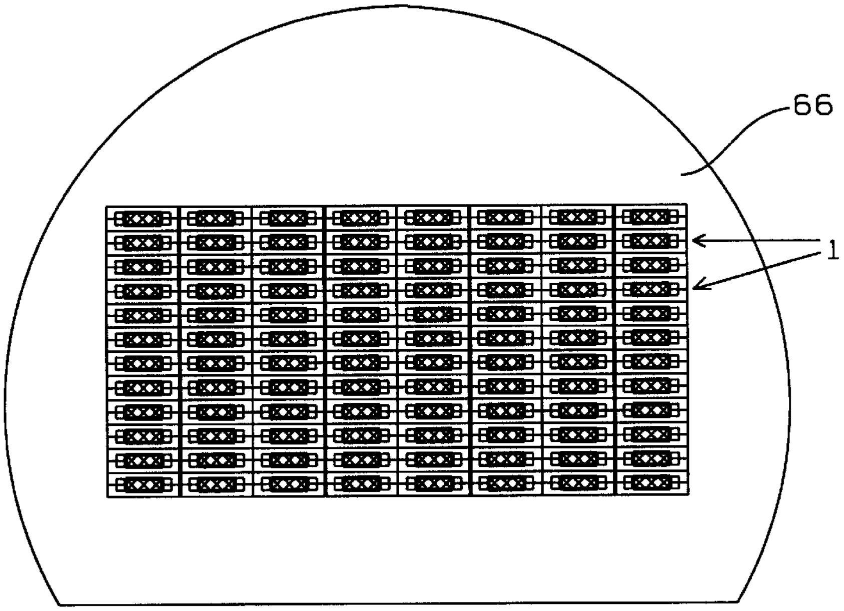
FIG. 5 shows a full population of cycling chambers covering an entire wafer.

Referring now to FIG. 4, shown there is an example of several chambers integrated to form a single multi-sample recycling unit. As can be seen, the individual chambers 11 are positioned inside the interior open area of silicon frame 1 and are connected to it through silicon beams 10. It is important to note that, except for these beams, the chamber is always thermally isolated from the frame by open space 3 (shown as a thin slot in FIG. 2). FIG. 5 shows how the sub-structure seen in FIG. 4 appears when full wafer 66 of silicon has been used to form multiple chambers.

Returning once more to FIG. 1*c*, as can be seen, the part of the chamber between valves 8 (where the actual temperature cycling occurs) is effectively a sandwich between glass plate 2 and silicon membrane 12 which is only between about 30 and 100 microns thick. This arrangement enables the physical volume (less than about 100 micro-liters) and thermal capacitance of the chamber to be kept to a minimum.

Figure 6:
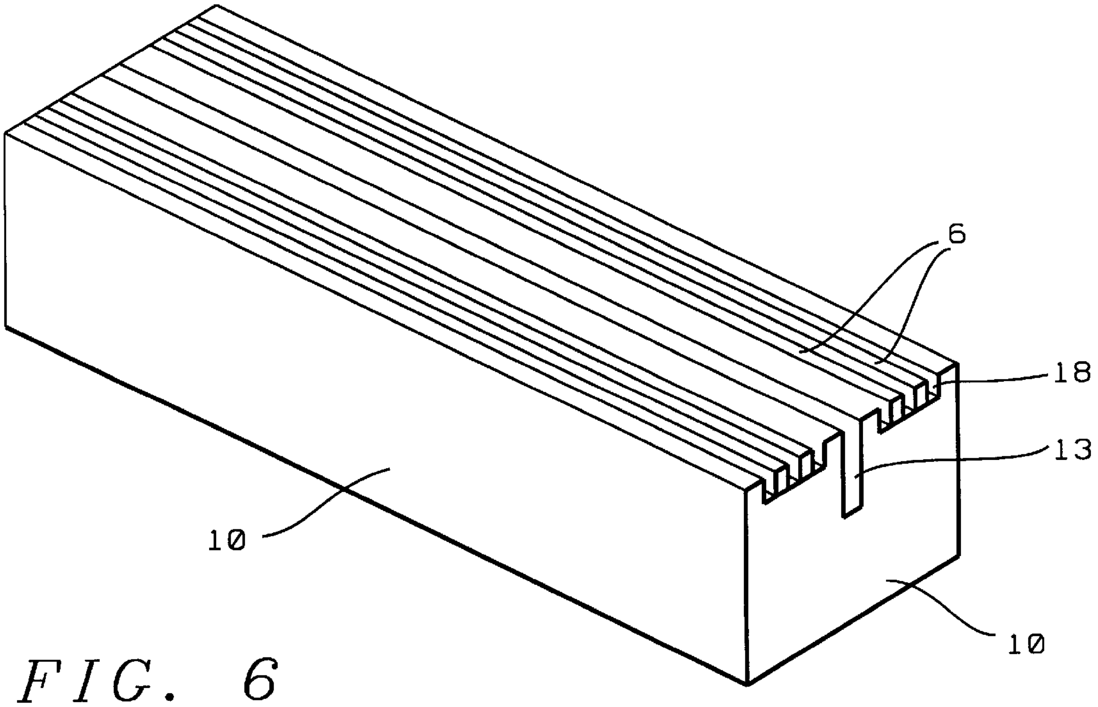
FIG. 6 illustrates how the resistor strips may be located inside slots in a conductive silicon beam.

Also seen in FIG. 1*b* are bonding pads 6. These facilitate the bonding of glass sheet 2 to the silicon. As a feature of the present invention these pads are placed inside trench 18 as illustrated in FIG. 6. These facilitate the application of anodic bonding to our structure. Anodic bonding is an excellent bonding technique that allows high stability at high temperature in various chemical environments as no polymer is used. The silicon and glass wafers are heated to a temperature (typically in the range 300–500° C. depending on the glass type) at which the alkali metal ions in the glass become mobile. The components are brought into contact and a high voltage applied across them. This causes the alkali cations to migrate from the interface resulting in a depletion layer with high electric field strength. The resulting electrostatic attraction brings the silicon and glass into intimate contact. Further current flow of the oxygen anions from the glass to the silicon results in an anodic reaction at the interface and the result is that the glass becomes bonded to the silicon with a permanent chemical bond.

Note that although we exemplify sheet 2 as being made of glass, other materials such as rigid plastics, fused quartz, silicon, elastomers, or ceramics could also have been used. In such cases, appropriate bonding techniques such as glue or epoxy would be used in place of anodic bonding.

Finally, in FIGS. 1*b* and 1*c* we note the presence of heat sink 14 to which the silicon frame 1 is thermally connected. An important advantage of this arrangement is that silicon substrate 1 can be kept close to room temperature rather than near the temperature of the reaction chamber during heating. This facilitates integration of the PCR thermocycler with other parts of micro total-analysis-system (PTAS) on a single chip, as well as for multi-chamber reaction with independent thermal control, as discussed earlier.

Second Embodiment

Figure 7B:
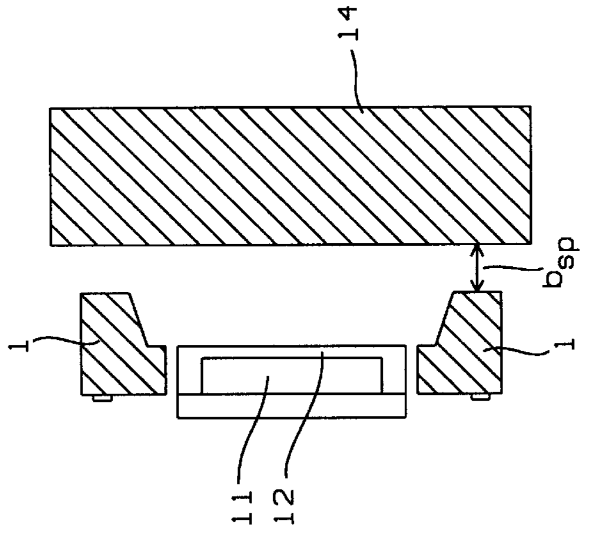
FIGS. 7*b* and 7*c* are orthogonal cross-sections taken through FIG. 7*a*.
Figure 7A:
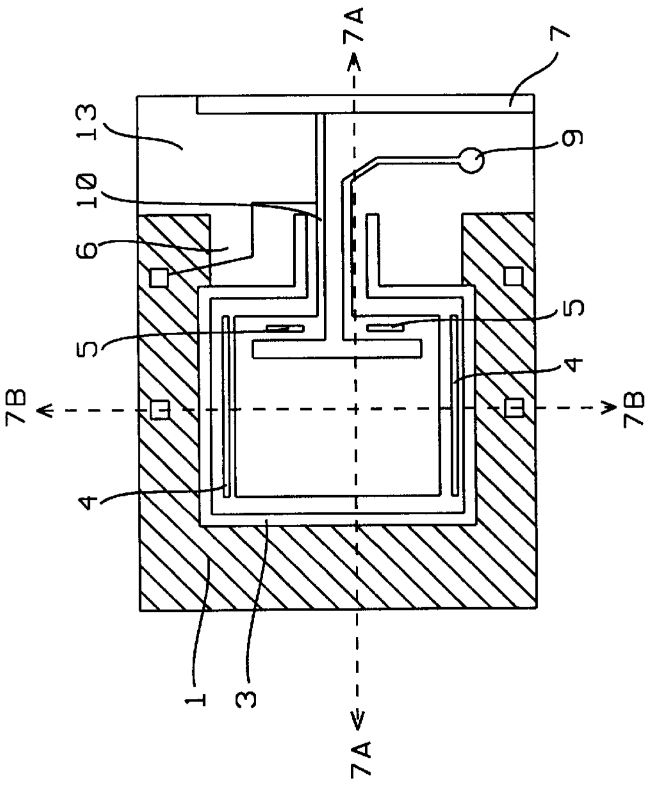
FIG. 7*a* shows a plan view of a second embodiment of the invention.
Figure 7C:
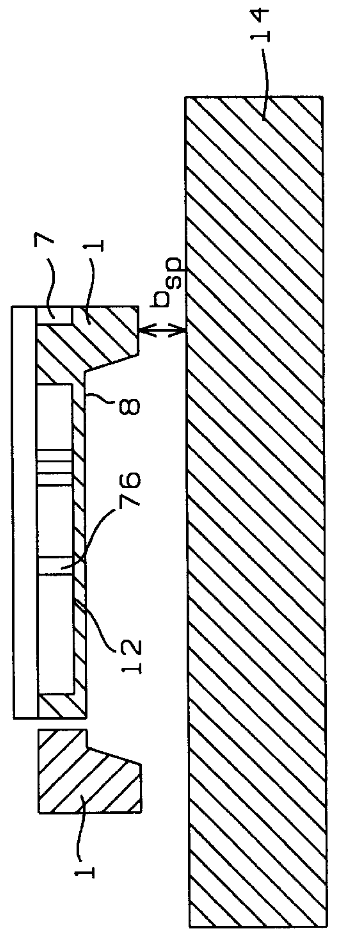

The second embodiment of the invention is generally similar to the first embodiment except that, instead of being connected to the silicon frame through two silicon beams, only a single cantilever beam is used. This has the advantage over the first embodiment that elimination of asymmetry due to fabrication/packaging and heating is achieved, resulting in easier control and uniformity of temperature. It is illustrated in FIGS. 7*a–c* and, as just noted, most parts marked there are the same as those shown in FIGS. 1*a–c*.

Since there is only one silicon beam available, it has to be used for both introducing as well as removing liquid to and from the chamber. This has been achieved by the introduction of baffle 76 that is parallel to the surface of the chamber (at the transfer area) and that is orthogonally connected to the transfer area by a sheet of material 84 that serves to separate incoming from outgoing liquid. Its action can be better seen in the closeup provided by FIG. 8. As in the first embodiment, liquid from common reservoir 7 is sent along channel 31 into the chamber. An air injector is also used to accomplish this although it is not shown in this figure. When the incoming liquid enters the chamber it is directed by baffle 76 to flow in direction 81.

Figure 8:
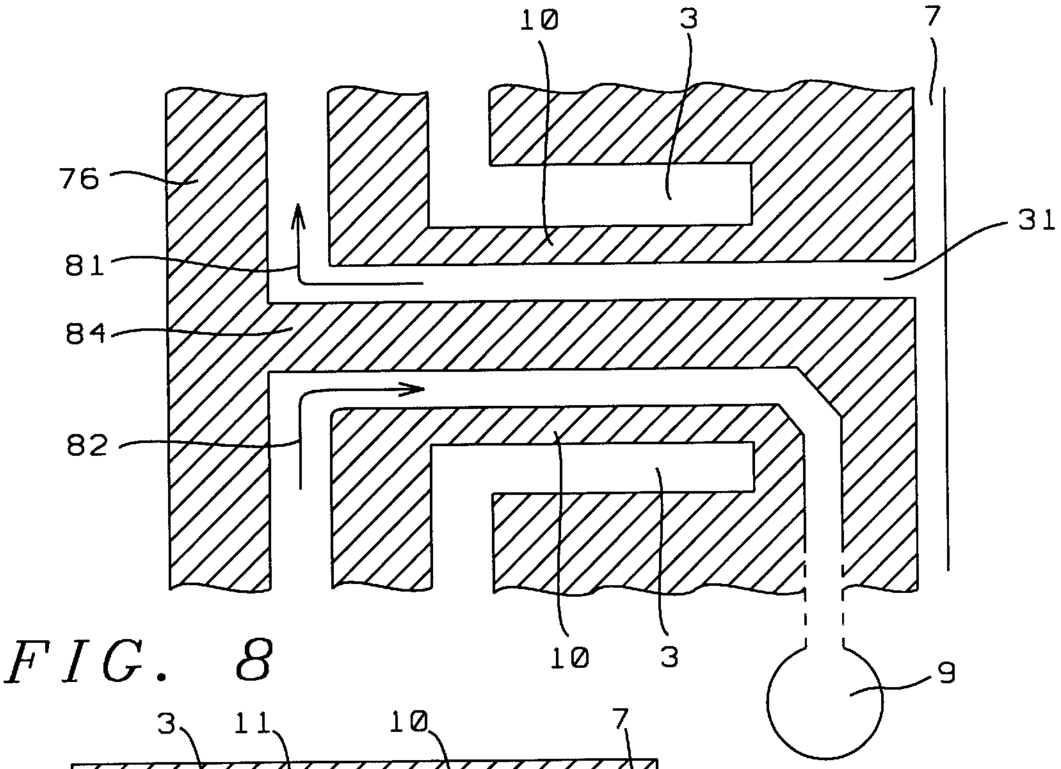
FIG. 8 is a closeup view of a portion of FIG. 7*a*.

Emptying of the chamber is accomplished in a similar manner to that of the first embodiment except that local sample reservoir 9 is on the same side as the inlet reservoir 7. When the chamber is to be emptied, baffle 76 again directs the flow of liquid, this time in direction 82. Seen in FIG. 7*c*, but not shown in FIG. 8, is valve 8. There are, of course, two such valves, as in the first embodiment, but the one that can be seen is blocking a view of the other one.

Figure 9:
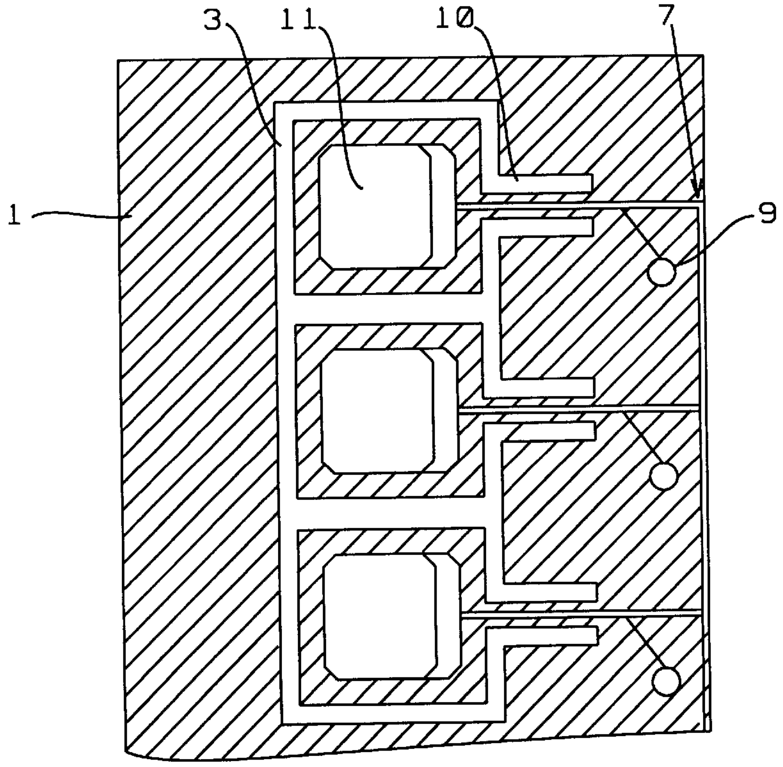
FIG. 9 is the equivalent of FIG. 1 for the second embodiment.

FIG. 9 is analogous to FIG. 4 and illustrates a group of three cycling chambers 11 suspended within the interior open area of silicon frame 1 which is itself part of a full silicon wafer.

Process for Manufacturing the Invention

We now describe a process for manufacturing the frame portion of the structure of the invention. Before proceeding we note that all figures that follow (FIGS. 10–15) show only the right hand side of the chamber but, since the left side is a mirror reflection of the right side, the process for manufacturing the entire chamber is readily envisaged.

Figure 10:
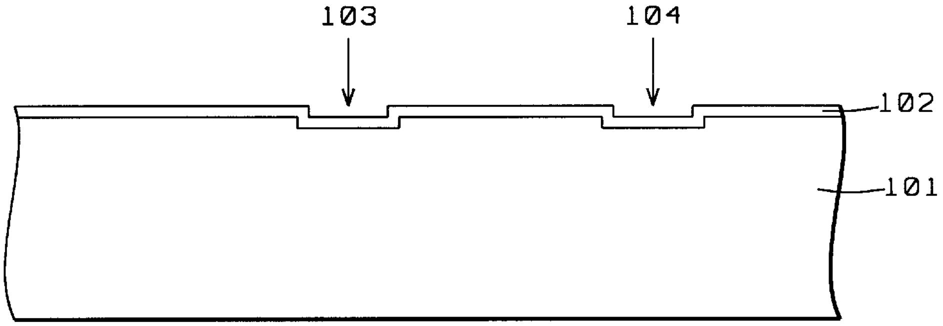
FIG. 10 shows the starting point for the process of the present invention.

Referring now to FIG. 10, process begins with the provision of silicon wafer 101, between about 350 and 700 microns thick, in whose upper surface, two inner trenches 103 and two outer trenches 104 are etched to a depth of between about 0.1 and 1 microns. The width of inner trenches 103 is between about 20 and 500 microns while that of outer trenches 104 is between about 50 and 500 microns.

Next, dielectric layer 102 is formed over the entire surface. Its thickness is between about 0.02 and 0.5 microns. Our preferred material for dielectric layer 102 has been silicon oxide formed by thermal oxidation or CVD (chemical vapor deposition) but other materials such as phosphosilicate glass (PSG), silicon nitride, polymers, and plastics could also have been used.

Figure 11:
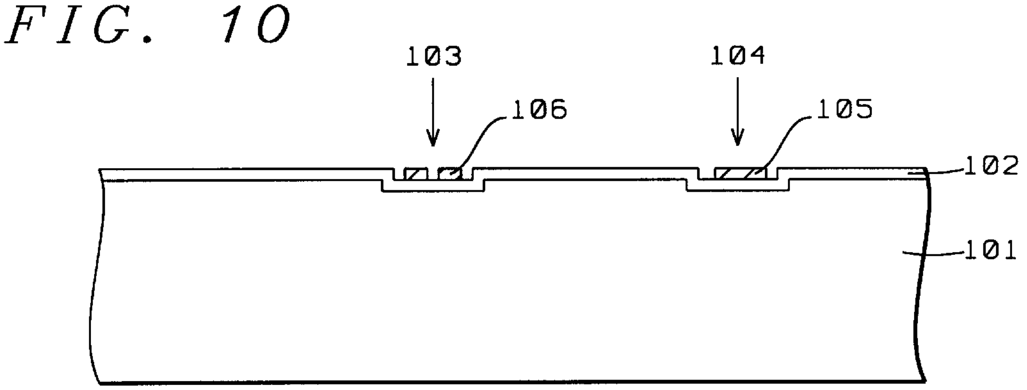
FIGS. 11 and 12 illustrate formation of resistive heaters and temperature sensors.

Next, as seen in FIG. 11, a layer of a material that is suitable for use as a temperature sensor (thermistor) 105 and also as a resistive heater is deposited to a thickness between about 1,000 and 10,000 Angstroms. Our preferred material for this has been aluminum but other materials such as gold, chromium, titanium, or polysilicon could also have been selected. This layer is then patterned and etched to form temperature sensors and the heater element. Bonding strips 106 are also shown.

Figure 12:
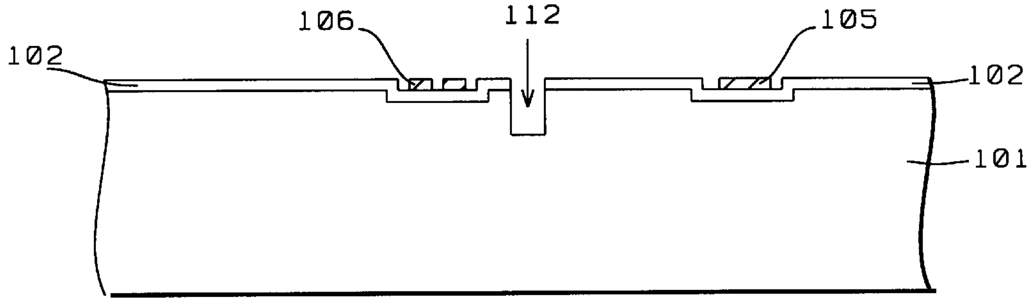

Moving on to FIG. 12, two top preliminary trenches 112 are then etched into the top surface to a depth of between about 30 and 100 microns and a width of between about 20 and 100 microns. The trenches 112 are located between inner trenches 103 and outer trenches 104, each about 100 microns from the inner trench.

Figure 13:
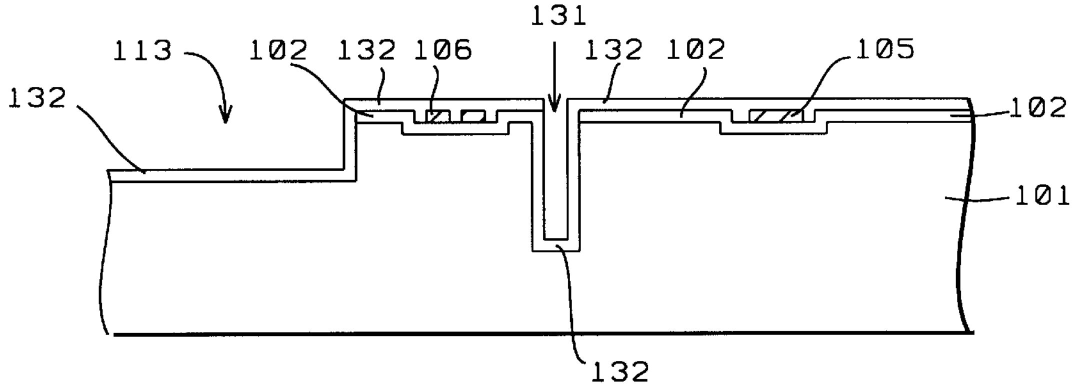
FIGS. 13 and 14 illustrate the formation of the silicon membrane and etch-through slots that are needed to achieve a high level of thermal isolation for the chamber.

Next, as seen in FIG. 13, the upper surface of the wafer is patterned and etched to form chamber trench 113. This is centrally located between the inner trenches 103 and is given a depth between about 30 and 500 microns and a width between about 100 and 10,000 microns. Trench 112 is not protected while trench 113 is being formed so that at the end of this step in the process, its depth will have increased. Also at this stage, second dielectric layer 132 is formed on all surfaces that don't already have a dielectric layer on them. Its thickness is between about 1,000 and 5,000 Angstroms. In FIG. 13, the newly extended and lined trench 112 is now designated as trench 131. Its depth is between about 60 and 600 microns.

Figure 14:
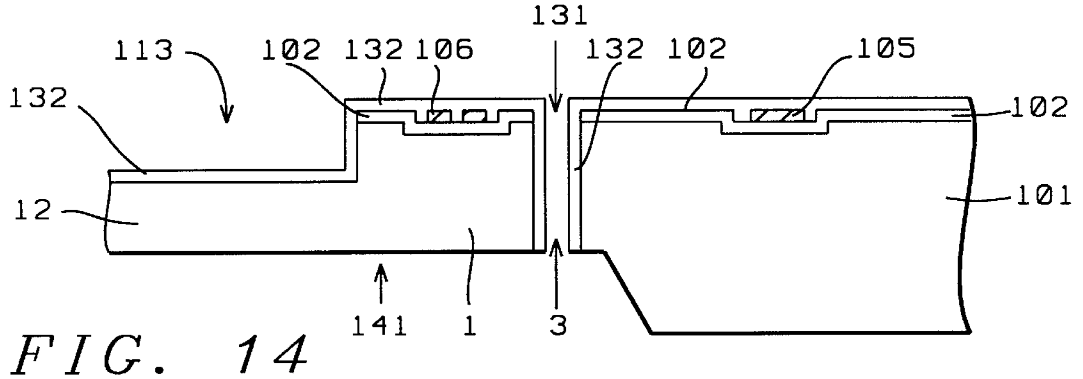

Referring now to FIG. 14, the lower surface of the wafer is patterned and etched to form under-trench 141. This is wide enough to slightly overlap the top preliminary trenches 131 and it is deep enough so that, at the completion of this step, trench 131 will be penetrating all the way through to the wafer's under-side and the wafer thickness (under trench 113) will have been reduced to between about 30 and 100 microns. In this way, silicon membrane 12 and frame 1, as shown in earlier figures, will have been formed.

Figure 15:
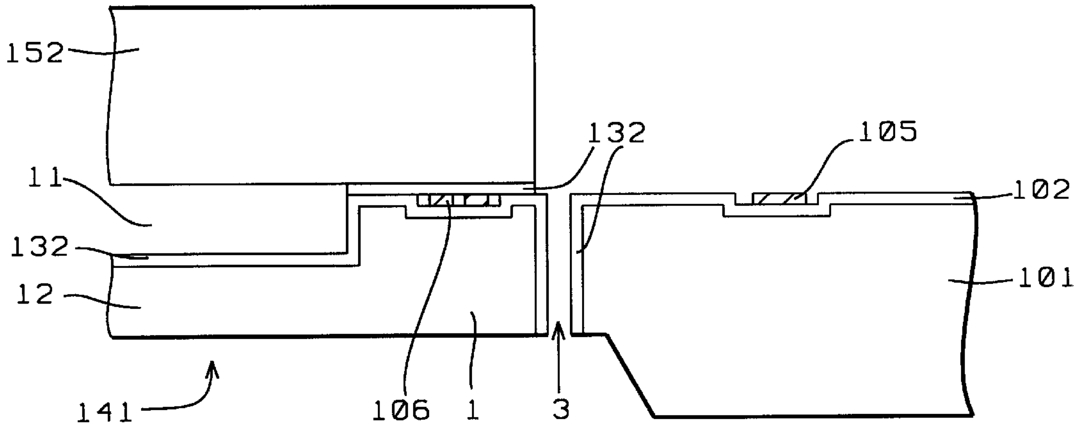
FIG. 15 shows how a sheet of dielectric material is bonded to the top surface to form the chamber.

The final step in the process is illustrated in FIG. 15. Sheet of dielectric material 152 is micro-machined to form holes in selected locations (as an example, see 9 in FIG. 1) and then bonded to the wafer to form a hermetically sealed chamber that is thermally isolated from the wafer by slot 3. For sheet 152, our preferred material has been glass which we then bonded to the wafer by means of anodic bonding. However, as noted earlier, other materials such as rigid plastics, fused quartz, silicon, elastomers, or ceramics could also have been used. In such cases, appropriate bonding techniques such as glue or epoxy would be used in place of anodic bonding. Finally, an etching step is used to remove the second dielectric layer 132 in the open areas that contain bond-pads for electrical connections.

Connecting the Array to the Outside World

Figure 16:
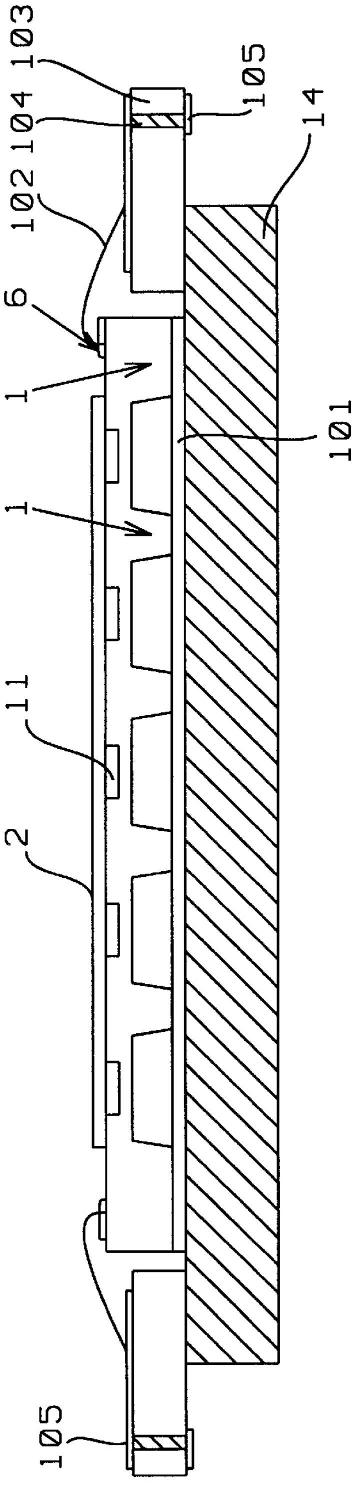
FIG. 16 illustrates how connection to the outside world may be made to an array of recycling chambers.

FIG. 16 shows the first of two possible ways to arrange the multi-chamber thermal cycler relative to the heat sink 14 and the electric lead-outs. In both ways, the thermal cycler array is mounted onto heat sink 14 with a thin layer of thermally conductive soft material 101 for better mechanical and thermal contact. This is to ensure that the local substrate 1 has very small thermal resistance to the heat sink 14 everywhere. Suitable materials for layer 101 include thermal conductive tapes, greases, glues, polymers, elastomers, rubber, and plastics. The thickness of layer 101 is typically between about 1 and 100 microns and its thermal conductivity is between about 0.2 and 20 W/m.K. It has a softness value between about 1 and 100 units on a Shore D Durometer.

Electric bond-pads 6 can be connected to the connectors 105 (metal pads/tracks) on the controller board 103 (e.g. a printed circuit board or PCB) through wire-bonding to probing-card 102.

Figure 17:
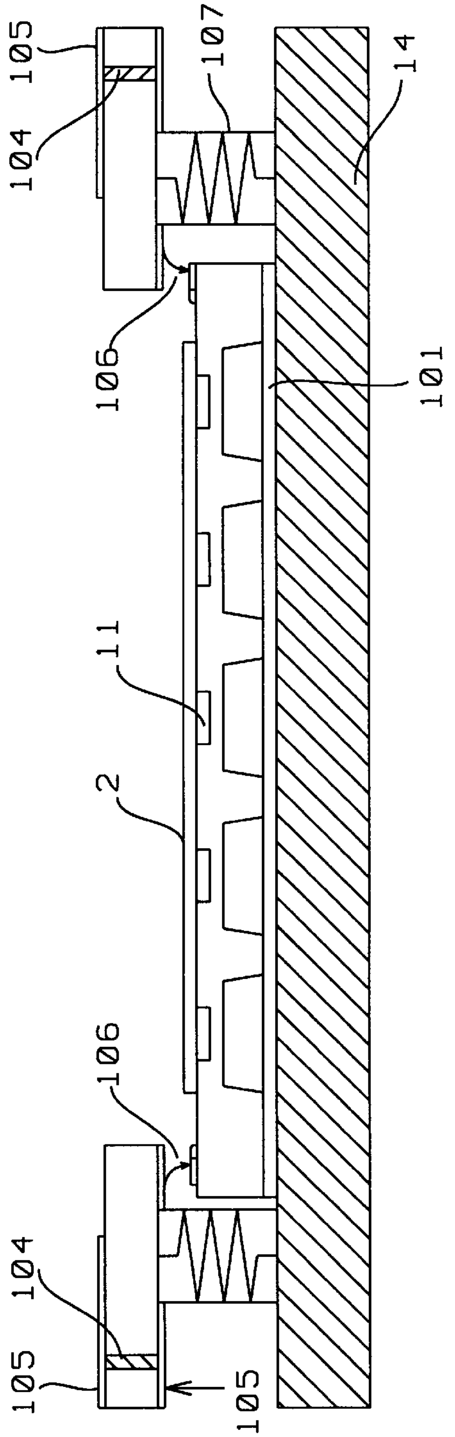
FIG. 17 shows another approach to making connection to the outside world for an array of recycling chambers.

Metal lead-outs can be on top or on bottom side of the controller board 103, or on both sides, connected through via 104. Or the bond-pads 6 can be conducted out to the controller board 103 through a fixture of the type shown in FIG. 17), where flexural electric connector 106 (e.g., probe/tip/bump) from the board 103 can be pressed directly on top of the corresponding bond-pads 6 on the thermal cycler chip. Additionally, the spacer 107 can be made flexible in the thickness direction for better mechanical contact between the connectors 106 from the controller board 103 and the bond-pads 6 from the thermal cycler chip.

Figure 18:
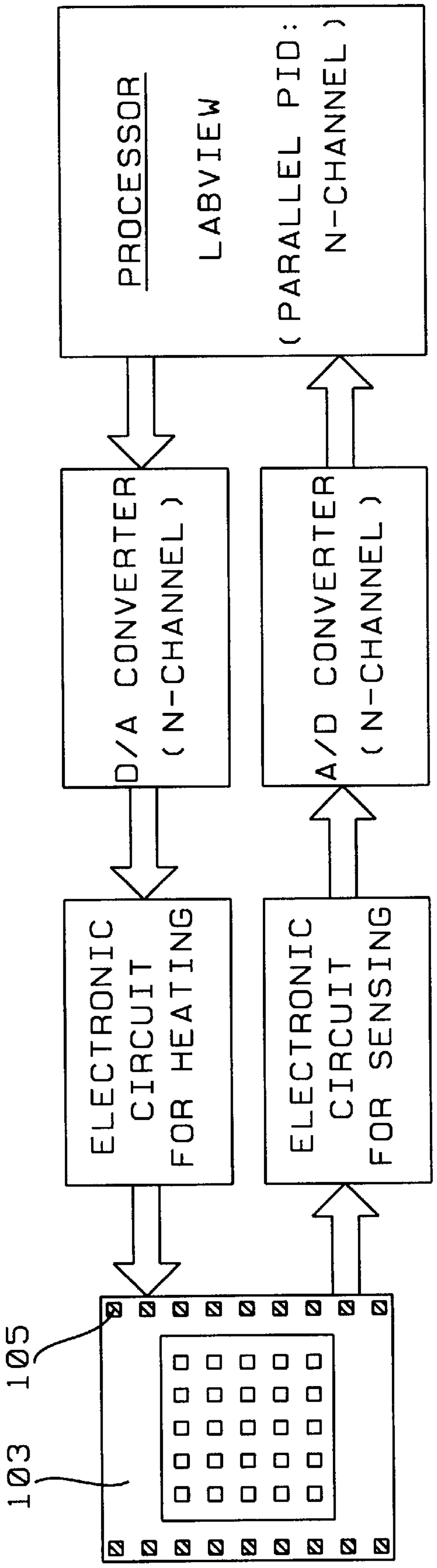
FIG. 18 schematically shows the flow of information into and out of the array.

FIG. 18 illustrates the configuration of the control system for multi-chamber independent thermal protocol control. Connectors 105 on the controller board 103 for all the sensors of the N-chamber thermal cycler are directed to the electronic circuit for temperature sensing. Typically, at least one sensor and one heater are needed for each chamber. Then the analog outputs of the sensors (at least N channels) are translated into digital data through analogue-to-digital (A/D) converter and sent to the processor (or computer). A LabView programmed multi-channel parallel PID (proportional-integral-derivative) controller, for example, will manage to follow the expected thermal protocols for the N chambers through the real-time updated/refreshed output signals for the (at least) N-channel heaters. These signals flow to the electronic circuit for updated/refreshed heating, after conversion to analogue signals in the DIA converter (having at least N-channels). Consequently this is a close-loop multi-channel parallel processing control system, particularly for multi-chamber thermal cyclers having independent multiplexing or parallel processing. The number of channels, N, will generally be from 2 to 96 or 2 to 384, when used in current macro thermal cycler machines.

Results

By using the above described structures and manufacturing process, we have been able to both build and simulate units that meet the following specifications:

| | |
|---|---|
| Heating power: <1.7 Watt; | Heating voltage: 8 volts |
| Ramp rate: 15–100° C/s; | Cooling rate: 10–70° C./s |
| Temperature uniformity: < ±0.3° C. (accuracy ± 0.2° C.) | |
| Cross-talk: <0.4° C. at 95° C. | |

The effectiveness of the units for Micro PCR use reaction was verified with the Plasmid/Genomic DNA reaction and agarose gel electrophoresis. The result was adequate amplification in a reduced reaction time relative to existing commercial PCR machines. It was also confirmed that the units may be reused after cleaning.

While the invention has been particularly shown and described with reference to the preferred embodiments thereof, it will be understood by those skilled in the art that various changes in form and details may be made without departing from the spirit and scope of the invention. The miniaturized thermal cycler of the present invention may, for example, be used as a thermal cycling chamber for various types of biological and/or chemical reactions.

What is claimed is:

1. A multi-chamber thermal cycler system, comprising:

a multi-chamber thermal cycler chip;

a layer of a material having high thermal conductivity as well as a high level of softness, said layer being uniquely located between the thermal cycler chip and a heat sink, whereby good thermal contact and conductance between the chip and the heat sink are provided;

a controller board, having opposing sides, that includes electrically conductive lines and tracks and electric connectors;

means for connecting and disconnecting bond-pads on the chip to the controller board; and a control system for multi-channel independent parallel protocol control, including: electronic circuits for multi-channel analogue and digital signals communication between the controller board and a processor having programmed multiple channel parallel proportional-integral-derivative control.

2. The multi-chamber thermal cycler system described in claim 1 wherein said layer is selected from the group consisting of thermal conductive tapes, greases, glues, polymers, elastomers, rubber, and plastics.

3. The multi-chamber thermal cycler system described in claim 1 wherein said layer has a thickness between about 1 and 100 microns.

4. The multi-chamber thermal cycler system described in claim 1 wherein said layer has a thermal conductivity between about 0.2 and 20 W/m.K.

5. The multi-chamber thermal cycler system described in claim 1 wherein said layer has a softness value between about 1 and 100 shore D Durometer units.

6. The multi-chamber thermal cycler system described in claim 1 wherein said electric connectors are on both sides of the board or on either side of the board.

7. The multi-chamber thermal cycler system described in claim 1 wherein said means for connecting and disconnecting bond-pads on the chip to the controller board is selected from the group consisting of wire-bonding, probing-cards and flextural electric connectors.

8. The multi-chamber thermal cycler system described in claim 1 wherein said multiple channel parallel proportional-integral-derivative control contains between 2 and 384 channels.

* * * * *